United States Patent [19]

Atkinson

[11] Patent Number: 4,765,588
[45] Date of Patent: Aug. 23, 1988

[54] CHECK VALVE FOR USE WITH A SYRINGE

[75] Inventor: Gordon E. Atkinson, Cederville, Ohio

[73] Assignee: Vernay Laboratories, Inc., Yellow Springs, Ohio

[21] Appl. No.: 897,231

[22] Filed: Aug. 18, 1986

[51] Int. Cl.⁴ .............................................. F16K 21/04
[52] U.S. Cl. .................... 251/149.1; 137/850; 604/256
[58] Field of Search ............... 137/843, 844, 846, 850; 141/350; 604/99, 167, 256; 251/149.1

[56] References Cited

U.S. PATENT DOCUMENTS

| | | | |
|---|---|---|---|
| 3,308,798 | 3/1967 | Snider | 137/846 |
| 3,601,151 | 8/1971 | Winnard | 137/846 |
| 3,831,629 | 8/1974 | Mackal et al. | 137/843 |
| 3,837,381 | 9/1974 | Arroyo | 251/149.1 X |
| 3,889,675 | 6/1975 | Stewart | 137/846 |
| 4,341,239 | 7/1982 | Atkinson | 137/846 |
| 4,387,879 | 6/1983 | Tauschinski | 137/846 |
| 4,566,493 | 1/1986 | Edwards et al. | 137/846 |

FOREIGN PATENT DOCUMENTS

| | | | |
|---|---|---|---|
| 1149727 | 12/1957 | France | 137/846 |
| 2337670 | 8/1977 | France | 604/256 |
| 1078650 | 8/1967 | United Kingdom | 604/99 |
| 1344166 | 1/1974 | United Kingdom | 604/167 |

Primary Examiner—Robert G. Nilson
Attorney, Agent, or Firm—Biebel, French & Nauman

[57] ABSTRACT

A check valve for sealing a fluid supply while permitting selective withdrawal of fluid includes a tubular side wall defining an insertion end and a supply end. A diaphragm is connected to the side wall and extends across the tube interior to close the interior. The diaphragm defines a slit therein extending diametrically across the diaphragm. The diaphragm is defined as a concave surface toward the insertion end of the side wall. A housing secures the side wall, encloses the supply end thereof, and exposes the insertion end. A port extends through the housing to communicate with the supply end.

9 Claims, 1 Drawing Sheet

CHECK VALVE FOR USE WITH A SYRINGE

BACKGROUND OF THE INVENTION

The present invention relates to check valves, and more particularly, to a check valve which is specifically adapted for use with a medical syringe. The check valve may be used to close a fluid conduit or container. The syringe may be inserted into the valve to withdraw fluid from the conduit or container.

In providing medical treatment to patients, it is often necessary to administer medications and other fluids to the patient using a syringe equipped with a needle. To prevent contamination, the needle should not be installed upon the syringe until immediately before insertion of the needle into the patient's body. As a result, it is preferred that the syringe not be filled by inserting the needle tip into the container of medication of other fluid. To accomplish this, the syringe is filled without the needle or other attachment mounted at its distal end.

Fluid is often withdrawn into the syringe from a bulk container. In large institutions such as hospitals a number of syringes are often filled by a single technician working in a central medicine supply area. In such environments, the fluid may be held within an elevated container, with a conduit extending from the container to the work area. The conduit is closed by a valve which normally prevents fluid from emerging from the conduit. Fluid may be drawn into the syringe upon connnecting the syringe with the valve.

One common type of valve for use in such a manner is a conventional stopcock. Such a valve includes a port for connection to the fluid supply and a port which is selectively connectible to the distal end of a syringe to be filled. A rotary valving portion is disposed in the flow path, and is movable between an open position and a closed position. After a syringe has been connected to the valve, the rotary portion is turned, typically via a handle, to permit fluid flow.

Because such a valve includes moving parts, great care must be taken in manufacturing the valve. More importanting, since the valving mechanism, i.e., the rotary portion, is mounted internally, the valve cannot be effectively cleaned.

A second type of check valve which could be used for closing such a fluid supply conduit is shown in U.S. Pat. No. 3,831,629, issued Aug. 27, 1974 to Mackal et al. Such a valve is often used in the inflation of urethral catheters. The valve includes a sleeve-like body including a rear portion and a relatively narrow forward portion, the junction between the portions defining a sealing surface. A plug-like valve element is disposed within the body, and is urged forward by an elastomeric rear portion connecting the valve element with the valve body. The element is held in contact with the sealing surface, thereby closing the fluid conduit. When the distal end of the syringe is inserted into the forward portion of the valve body, it contacts the valve element. This in turn moves the element rearwardly, opening a fluid passage around the valve element.

One disadvantage with the check valve disclosed in Mackal et al is the tortuous path which the fluid must follow as it passes around the valve element. For example, where the fluid is blood, the red blood cells can be damaged as they bump against each other and the valve elements and valve body walls while moving around the elements within the valve. Even in the case of a medications, the pressure drop as the fluid passes the valve element may introduce air into the fluid or may otherwise detrimentally agitate the solution.

What is needed, therefore, is a check valve for use in conjunction with a syringe for withdrawing fluids from a supply container. Such a valve should eliminate the problem noted above by providing for easy cleaning of the valve, and by defining a straight flow path for the fluid with no appreciable pressure drop. The valve should be capable of quickly be resealed, and should be sufficiently inexpensive that the valve assembly is disposable.

SUMMARY OF THE INVENTION

The present invention provides a valve for use in sealing a fluid supply while permitting selective withdrawal of fluid. The valve is particularly adapted for use in conjunction with a medical syringe for withdrawing fluid from the supply.

The valve includes a tubular side wall defining an insertion end, a supply end and a tube interior. A diaphragm is connected to the side wall and extends across the tube interior to close the interior. The diaphragm is located along the tube interior remote from the supply end and the insertion end. The diaphragm defines a slit therein extending diametrically across the diaphragm, and also defines a concave surface thereon toward the insertion end.

A housing means is provided for securing the side wall. The housing means encloses the supply end and defines a port that extends through the housing means and communicates with the supply end. The housing means is further defined to expose the insertion end.

The concave surface defined by the diaphragm may be cylindrical. In such a case, the cylindrical concave surface defines an axis, with the axis being parallel to the slit. The diaphragm is preferably of a substantially uniform thickness, so that a convex surface is defined on the diapragm toward the supply end.

The tubular side wall may be cylindrical, and the side wall and the diaphragm may be formed as a single piece from an elastomeric material.

The housing means may define a supply conduit extending outwardly from the housing means in fluid communication with the port.

A flange is defined about the side wall at the supply end, with the housing means defining a groove therein for containing the flange, whereby the side wall is secured into the housing.

The housing means may include an inlet portion defining a cover plate disposed over the supply end of the tubular side wall and against the flange, with the port extending through the plate to open into the tube interior. A restraining portion is connected to the inlet portion and has a central opening for passage of the tubular side wall therethrough. The inlet portion and the retaining portion are then connected together to define the groove for containing the flange. The retaining portion includes a ring member for defining the central opening and an annular collar extending about the periphery of the ring member, with the retaining portion being connected to the inlet portion along the annular collar.

Accordingly, it is an object of the present invention to provide a check valve for use in conjunction with a syringe for withdrawing fluids from a supply container; to provide such a valve that utilzes a straight flow path through the valve for the fluid; to provide such a valve that enable fluid to pass therethrough with no appreciable pressure drop; to provide such a valve that is easily opened by insertion of the syringe into the valve, and that securely and quickly reseals upon withdrawal of the syringe; and to provide such a valve that is simple and inexpensive.

Other objects and advantages of the present invention will be apparent from the following description, the accompanying drawings, and the appended claims.

DETAILED DESCRIPTION OF THE PREFERRED EMBODIMENT

Figure 1:
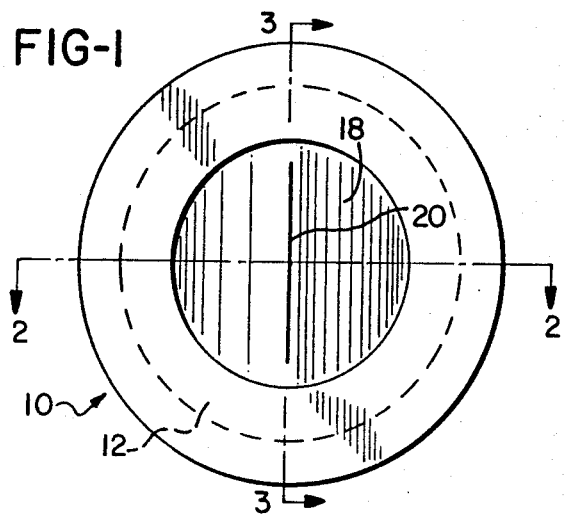
FIG. 1 is a plan view of the resilient valving member for the check valve in accordance with the present invention; taken from the inlet end of the valving member.
Figures 2, 3:
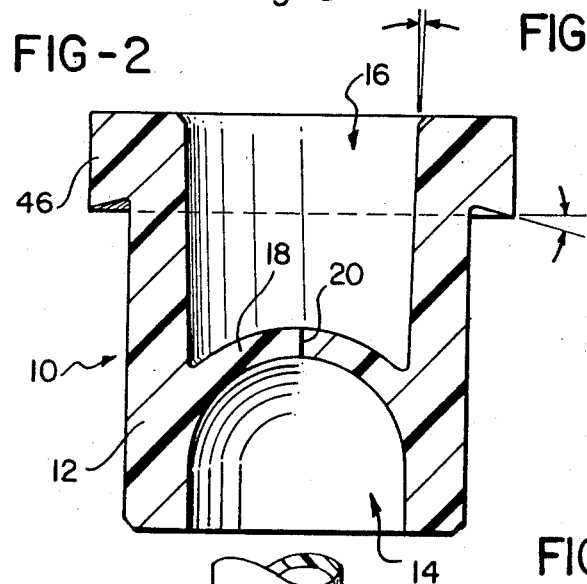
FIG. 2 is a sectional view of the valving member taken generally along line 2—2 of FIG. 1.
FIG. 3 is a sectional view of the valving member taken generally along line 3—3 of FIG. 1.

A check valve in accordance with present invention for use with a syringe is shown generally in the drawings, and the valving member may be particularly seen by reference to FIGS. 1, 2 and 3. The valving member 10 is formed as a single molded piece, constructed from a resilient elastomeric material such as rubber. The valving member 10 includes a cylindrical, tubular side wall 12, the side wall 12 terminating at one end in insertion end 14, and at the opposite end in a supply end 16. A slight inward taper is formed in side wall 12 from supply end 16.

A diaphragm 18 is connected to side wall 12 and extends across the tube interior so as to close off the interior. As best seen in FIG. 1, a slit 20 is formed in the diaphragm 18 and extends diametrically across the tube interior, terminating at each end short of side wall 12.

Referring now to FIG. 2, the valve member 10 is seen in a section taken transverse to slit 20. As can be seen, diaphragm 18 is located along the tube interior remote from both insertion end 14 and supply end 16. Further, the diaphragm defines a curved surface which is concave with respect to insertion end 14. It should also be noted that diaphragm 18 is slightly thicker near the junction with side wall 12, and tapers to a thinner section towards the center.

Diaphragm 18 is seen in FIG. 3 in a section taken along slit 20. In this direction, diaphragm 18 is not curved, and thus the preferred shape for diaphragm 18 can be described as cylindrical. However, diaphragm 18 could also be formed to be spherical or dome-like, i.e., having a curve along slit 20 that is generally similar to that transverse to the slit.

Figure 4:
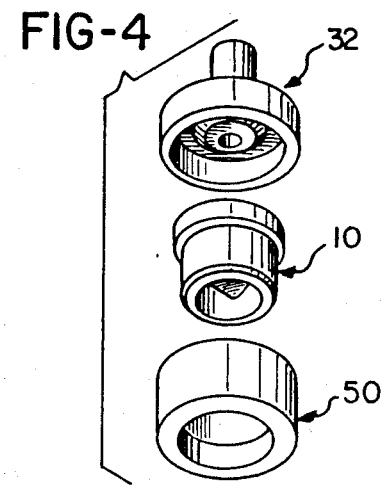
FIG. 4 is an exploded perspective view of the housing for the check valve of the present invention.
Figure 5:
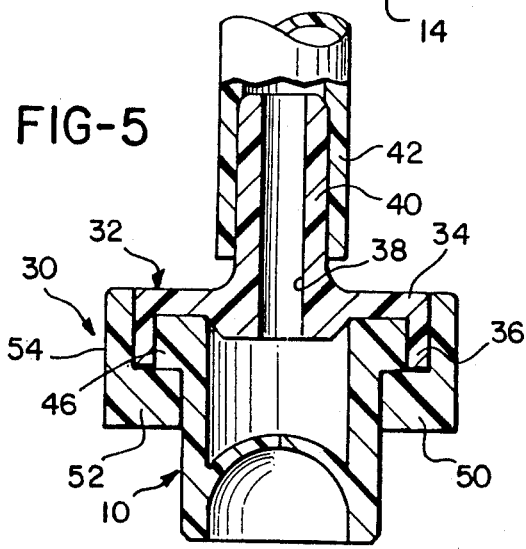
FIG. 5 is a view similar to FIG. 2, but showing the valving member mounted within the housing.

Valve member 10 is mounted within a two-part housing, the portions of which can be seen by reference to FIG. 4. The housing and valve member are shown in an assembled state in FIG. 5.

Housing 30 includes a support portion 32 including a circular plate 34 surrounded by an outwardly extending cylindrical flange 36. An inlet port 38 is defined through plate 34 and along a conduit 40 onto which may be secured a supply tube 42. A raised portion 44 is provided on plate 34, surrounding the opening to inlet port 38.

Referring briefly back to FIG. 2, valve member 10 includes annular flange 46 located around side wall 12 at the supply end 16. Flange 46 is formed with an inward bevel so that the flange is thicker at its outer end than adjacent to side wall 12.

Referring back to FIG. 5, valve member 10 is positioned with supply end 16 of side wall 12 located against base plate 34. Flange 46 of the valve member fits securely within flange 36 of the support portion 32. Raised portion 44 on base plate 34 and the slight inward taper of the tube interior cooperate to ensure a centered position for valve member 10 on support plate 34.

Valve member 10 is held in place along support portion 32 by a cover portion 50. Cover portion 50 includes annular cover ring 52 which is disposed along the surface of flange 46 of the valve member 10 not contained within support portion 32. A flange 54 extends from ring 52, and with ring portion 50 in position on support portion 32, flange 54 is located against flange 36 of portion 32. Contact of flanges 54 and 36 provides a surface along with the two portions may be secured together, such as by an adhesive or, more preferably, by ultrasonic welding.

As seen in FIG. 2, flange 46 is formed with an inward taper such that flange 46 is of greater height along its periphery than its innermost adjacent side wall 12. At its thickest, outermost portion, flange 46 is of a height slightly greater than the distance between ring 50 and support plate 34 when the housing portions are secured together. This causes flange 46 to be slightly compressed, when the housing is assembled, between ring 50 and support plate 34, but the tapered portion provides some open area into which the compressed, resilient rubber may move. This provides a more secure seal, since the forces generated during compression are isolated in the flange portion of the valving member 10. Further, no distorting forces will be transmitted through the side wall 12 to diaphragm 18, which could otherwise result in unwanted opening of slit 20.

In use, a supply container (not shown) holding a quantity of fluid such as medication is positioned in an elevated location. A tube or other conduit extends from the supply, and may be seen as tube 42 shown in FIG. 5. The valve assembly is located at the opening end of the tube. The fluid back pressure, along with the curved surface of the diaphragm, forces slit 20 to remain closed, thereby preventing fluid flow out of the tubing.

Figure 6:
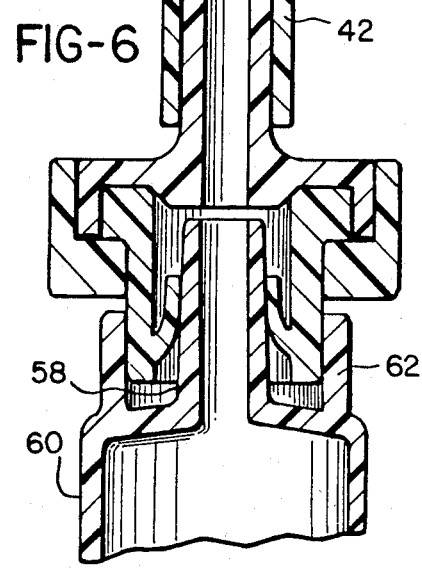
FIG. 6 is a view similar to FIG. 5, but showing the check valve with a syringe inserted thereinto for withdrawal of fluid.

To withdraw fluid into a syringe, as shown in FIG. 6, the distal end 58 of a syringe 60 is positioned against the diaphragm 18 of valve member 10. The syringe is inserted into the valve member 10, which pushes through the resilient diaphragm. Syringe 60 is then coupled into the fluid supply. Fluid may be withdrawn by the syringe, and it will be noted that the fluid path is straight and direct. Upon completion of filling of the syringe, the syringe is withdrawn from the valve member 10. The resilience of the elastomeric material of diaphragm 18 results in the return of the diaphragm to its original configuration, which return is aided by the fluid pressure of the fluid supply against the diaphragm. The valve is then sealed against any further fluid flow.

Syringe 60 may have a distal end provided with a luer-locking configuration, as shown in FIG. 6, including a cylindrical sleeve 62 on which the locking means (not shown) may be formed. In such a case, the insertion end 14 of side wall 12 may be provided with a slight chamfer, as best shown in FIG. 2, to facilitate fitting of the side wall end into sleeve 62.

It should be noted that the entire portion of the valve which comes into contact with the syringe, i.e., the outer surface of the diaphragm and the region of the side wall around insertion end 14, are clearly exposed. Thus, any cleaning of the valve member, including sterilization, can be easily and effectively carried out. In addition, any accidental dripping of fluid from the syringe as it is withdrawn from the valve will remain in the cup-like portion of the valve member defined by diaphragm 18 and side wall 12 near insertion end 14. Any such fluid may then be easily cleared away.

While the form of apparatus herein described constitutes a preferred embodiment of this invention, it is to be understood that the invention is not limited to this precise form of apparatus, and that changes may be made therein without departing from the scope of the invention which is defined in the appended claims.

What is claimed is:

1. A valve for use in sealing a fluid supply while permitting selective withdrawal of the fluid, comprising:
    a tubular side wall defining a first end, a supply end, a tube interior and a tube exterior;
    a diaphragm connected to said side wall and extending across said tube interior to close said interior, said diaphragm being located along said tube interior remote from said supply end and said first end;
    said diaphragm defining a slit therein extending diametrically across said diaphragm;
    said diaphragm defining a concave surface thereon toward said first end;
    housing means for securing said side wall and disposed in sealing contact with said side wall for sealing said supply end from said tube exterior, said housing means surrounding and enclosing said supply end and defining a port extending through said housing means and communicating with said supply end, said housing means terminating in contact with said side wall remote from said first end to expose said first end;
    a flange defined about said side wall at said supply end, said housing means defining a groove therein for containing said flange, whereby said side wall is secured into said housing means;
    said housing means including:
    an inlet portion closing said supply end of said tubular side wall and disposed against said flange, said port extending through said inlet portion to open into said tube interior; and
    a retaining portion connected to said inlet portion and having a central opening for passage of said tubular side wall therethrough;
    said inlet portion and said retaining portion being connected together to define said groove for containing said flange.
2. A valve as defined in claim 1, wherein said concave surface is cylindrical.
3. A valve as defined in claim 1, wherein said cylindircal concave surface defines an axis, said axis being parallel to said slit.
4. A valve as defined in claim 1, wherein said diaphragm further defines a convex surface thereon toward said supply end.
5. A valve as defined in claim 1, wherein said diaphragm is of a greater thickness adjacent said side wall than adjacent said slit.
6. A valve as defined in claim 1 wherein said tubular side wall is cylindrical.
7. A valve as defined in claim 1, wherein said side wall and said diaphragm are formed as a single piece from an elastomeric material.
8. A valve as defined in claim 1, further comprising a supply conduit extending outwardly from said housing means in fluid communication with said port.
9. A valve as defined in claim 1, wherein said retaining portion includes a ring member for defining said central opening and an annular collar extending about the periphery of said ring member, said retaining portion being connected to said inlet portion along said annular collar.

* * * * *